United States Patent [19]

Babb et al.

[11] 4,399,036

[45] * Aug. 16, 1983

[54] PROPORTIONING SYSTEM FOR BICARBONATE DIALYSATE

[75] Inventors: Albert L. Babb; Belding H. Scribner, both of Seattle, Wash.

[73] Assignee: Diachem, Inc., Arlington Heights, Ill.

[*] Notice: The portion of the term of this patent subsequent to Apr. 27, 1994, has been disclaimed.

[21] Appl. No.: 96,865

[22] Filed: Nov. 23, 1979

[51] Int. Cl.³ .................. B01D 31/00; B01D 13/00
[52] U.S. Cl. ............................. 210/638; 210/647; 210/96.2; 210/321.3
[58] Field of Search ............... 210/22 C, 22 A, 321 B, 210/96.2, 638, 647; 137/93.5; 423/424, 422, 423, 202

[56] References Cited

U.S. PATENT DOCUMENTS

| | | | |
|---|---|---|---|
| 3,532,102 | 10/1970 | Glassey | 137/93 X |
| 3,598,727 | 8/1971 | Willock | 210/22 |
| 3,743,598 | 7/1973 | Field | 137/5 X |
| 3,962,075 | 6/1976 | Fialkoff et al. | 210/22 C X |
| 4,153,554 | 5/1979 | Heide et al. | 210/137 X |
| 4,202,760 | 5/1980 | Sturey et al. | 210/647 X |
| 4,326,955 | 4/1982 | Babb et al. | 210/638 |

FOREIGN PATENT DOCUMENTS 2825134 12/1978 Fed. Rep. of Germany ..... 210/46.2

OTHER PUBLICATIONS

Sargent et al., Abstracts, Amer. Soc. ARDF Internal Organs, 6:75, 1977.
Kirkendol, et al, "A Comparison—Solutions", Trans. Am. Soc. ARDF Intern. Organs, vol. XXIII, 1977, pp. 399-405.
Gonzalez, et al., "On The—Hemodialysis," Trans. Am. Soc. ARDF. Intern. Organs, vol. XX, 1974, pp. 169-174.

Primary Examiner—Frank A. Spear, Jr.

[57] ABSTRACT

A proportioning system for compounding a bicarbonate-containing dialysate suitable for hemodialysis of human blood is disclosed. An aqueous alkali metal carbonate solution and an aqueous hydrochloric acid-containing solution are combined at a predetermined volumetric rate, and the conductivity as well as the hydrogen ion activity of the resulting bicarbonate-containing dialysate is monitored.

19 Claims, 3 Drawing Figures

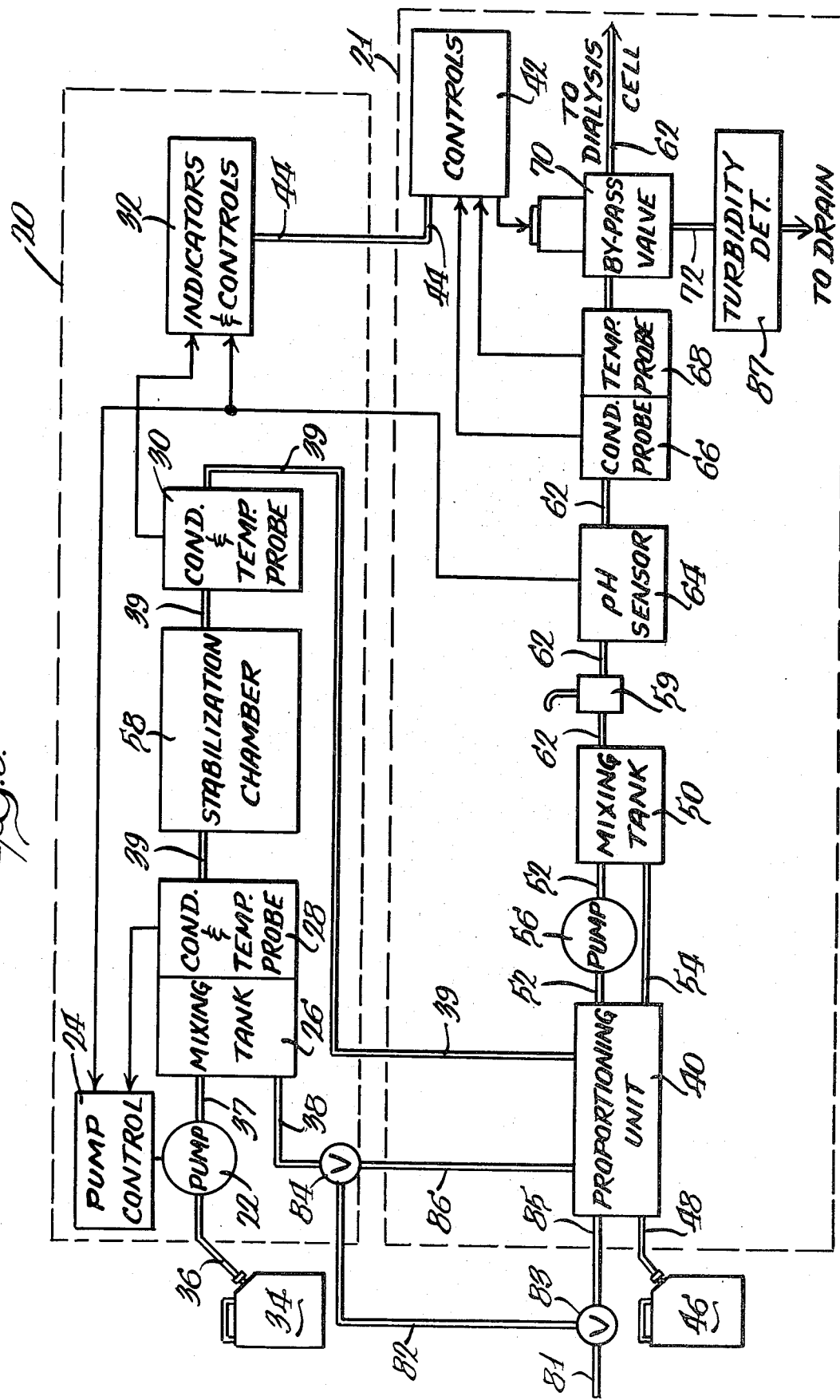

PROPORTIONING SYSTEM FOR BICARBONATE DIALYSATE

DESCRIPTION

Field of the Invention

This invention relates to hemodialysis and, in particular, to a system for dialyzing the blood of a patient across a semi-permeable membrane utilizing a dialysate that contains sodium bicarbonate.

BACKGROUND OF THE INVENTION

It has been recognized for some time that human blood may be conditioned through dialytic action with a selected exchange fluid.

Dialysis is performed on patients whose kidneys are not capable of adequate purification of blood and elimination of excess water. This is usually accomplished by circulating a portion of the patient's blood through a dialysis cell in which the patient's blood passes on one side of a semi-permeable membrane and a dialysate solution on the other side thereof. The semi-permeable membrane passes waste materials and water from the patient's blood to the dialysate.

Dialysis is literally a life-saving process; however, sometimes undesirable side effects such as hypotension, fatigue, nausea, and the like, are encountered. Research is continuing to counter the adverse side effects and to further improve the efficacy of hemodialysis, including investigations to improve the composition of the exchange fluid, i.e., the composition of the dialysate.

A dialysate is an aqueous solution of an alkalizing salt. In the early days of dialysis sodium bicarbonate was used as the alkalizing agent. Subsequently, sodium acetate was substituted for sodium bicarbonate as the alkalizing agent since sodium acetate metabolizes in the patient's body to sodium bicarbonate and also because aqueous sodium acetate solutions are more easily maintainable in a sterile condition.

With the advent of more efficient, large-surface area dialysis equipment, undesirable side effects have been observed when sodium acetate-based dialysates are utilized, however. For example, in Graefe et al., "Less Dialysis-Induced Morbidity and Vascular Instability with Bicarbonate in Dialyzate," Annals of Internal Medicine 88:332-336 (1978), it is disclosed that a sodium bicarbonate-containing dialysate causes less nausea, headache, vomiting, post-dialysis fatigue, hypotension, disorientation and dizziness than a sodium acetate-containing dialysate when used in a high-efficiency, large-surface area dialyzer. Additionally, a beneficial effect of a sodium bicarbonate-containing dialysate in reducing the incidence of atherosclerosis is recognized in Kluge et al., Int. Soc. Art. Arg. 3A, p. 23 (April 1979).

The foregoing articles suggest that sodium bicarbonate, rather than sodium acetate, should be the alkalizing agent of choice for dialysates. However, aqueous sodium bicarbonate solutions, unlike aqueous sodium acetate solutions, are not self-sterilizing and thus may present sterility problems when prepared in advance of dialysis.

A unique solution to the foregoing problem is proposed in our copending U.S. patent application U.S. Ser. No. 048,575, filed on June 14, 1979 but abandoned in favor of U.S. Ser. No. 209,742, filed on Nov. 24, 1980 that matured into U.S. Pat. No. 4,326,955 on Apr. 27, 1982, to wit, the generation of an aqueous, bicarbonate ion-containing dialysate on demand from bacteriostatic, stable aqueous solutions just prior to dialysis. In particular, sodium bicarbonate solution is generated in situ by the interaction of an aqueous sodium carbonate solution with an aqueous acid solution containing a dissolved acid which is a member of the group consisting of hydrochloric acid (HCl), acetic acid (HAc), and mixtures thereof. The formulation of sodium bicarbonate proceeds by the following steps:

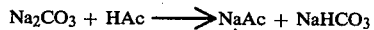

When a sodium bicarbonate-containing dialysate is prepared in the foregoing manner, it is desirable to have an effective and reliable means for metering and combining the respective starting acid and carbonate solutions to produce the sodium bicarbonate-containing dialysate. To this end the present invention provides a proportioning system that is eminently suitable for in situ generation of a bicarbonate-containing dialysate.

SUMMARY OF THE INVENTION

The present invention permits the in situ preparation of a bicarbonate-containing dialysate suitable for use in a dialysis machine from bacteriostatic starting solutions and also contemplates a proportioning system for such preparation. In the proportioning system, an aqueous hydrochloric acid-containing solution and an aqueous carbonate-ion containing solution are combined, and the conductivity as well as the hydrogen ion activity of the produced, bicarbonate-containing dialysate is monitored.

A preferred embodiment of the system of this invention includes a source of aqueous carbonate ion concentrate, a source of aqueous hydrochloric acid-containing concentrate, a source of physiologically tolerable water, and means for commingling an aqueous stream from each of the aforementioned sources to produce a bicarbonate-containing dialysate. Additionally, the system includes a potentiometric means for monitoring hydrogen ion activity in the produced dialysate and providing an output indicative of the hydrogen ion activity (e.g., a pH probe or meter), conductivity sensing means for monitoring the conductivity of the produced dialysate and providing an output indicative of the conductivity thereof, and a flow control means that is responsive to both of the foregoing outputs and is adapted to interrupt normal flow of the produced dialysate when the value of either of these outputs deviates from a set magnitude by a predetermined amount.

BRIEF DESCRIPTION OF THE DRAWINGS

In the drawings,

FIG. 3 is a block diagram of a preferred proportioning system embodying the present invention.

DESCRIPTION OF PREFERRED EMBODIMENTS

Figure 1:
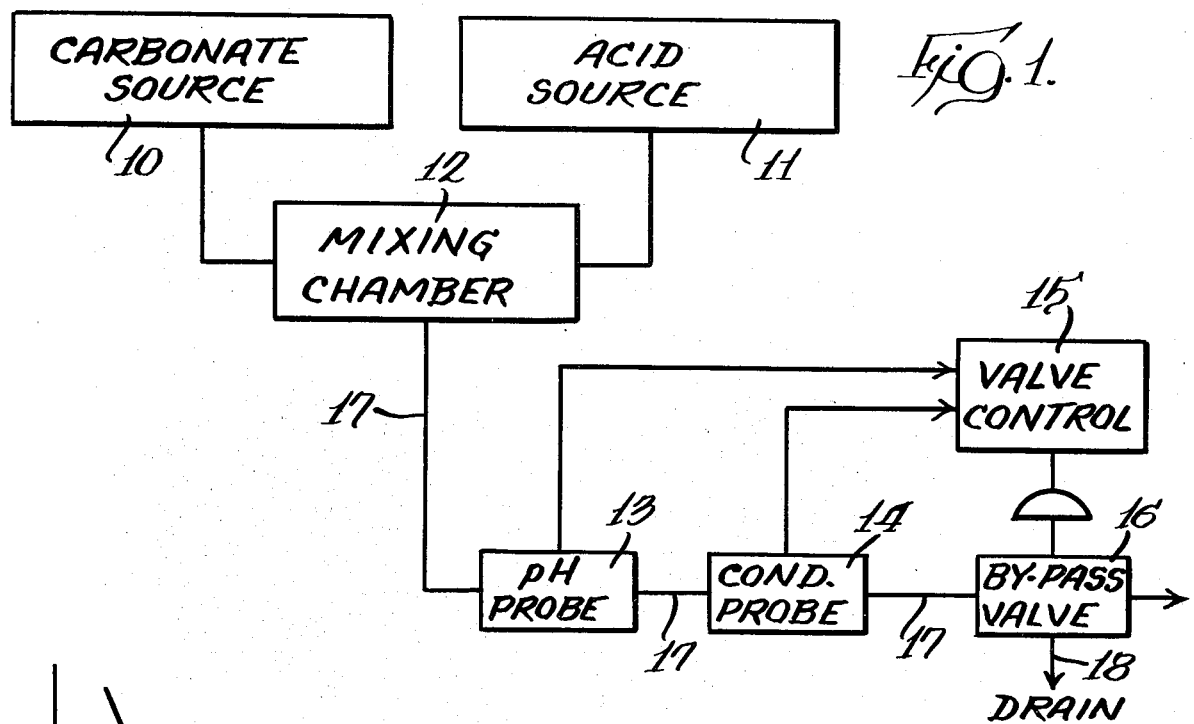
FIG. 1 is a block diagram illustrating a system embodying the present invention.

The basic elements of the present system are illustrated in FIG. 1. An aqueous stream from carbonate source 10 and an aqueous stream from acid source 11 are combined in mixing chamber 12. The carbonate source can be a supply of a water-soluble, physiologically tolerable alkali metal carbonate, e.g., sodium carbonate in anhydrous or hydrated form, dissolved in physiologically tolerable water such as conditioned water, e.g., deionized water, distilled water, or the like, at a concentration sufficiently dilute upon combination with the acid source so as not to bring about the precipitation of any insoluble carbonates upon addition of the aqueous acid solution that could otherwise result due to the presence of small amounts of cations such as calcium or magnesium that may be present in the acid solution.

The acid source can be a supply of hydrochloric acid alone or hydrochloric acid admixed with acetic acid in a predetermined ratio as presecribed by the attending physician. The acid is diluted with conditioned water, preferably to a hydrogen ion concentration of about 11 to about 12 Normal for the aqueous acid concentrate. Other constituents such as sodium chloride, calcium chloride, magnesium chloride, and the like, can also be dissolved therein.

Mixing chamber 12 is of sufficient holding capacity to provide adequate mixing and residence time for the carbonate-to-bicarbonate conversion to take place. If desired, a separate holding tank may be provided downstream of mixing chamber 12 for this purpose. Usually, a carbonate, e.g., $Na_2CO_3.H_2O$, solution is first prepared in a concentrated form, having a sodium carbonate monohydrate ($Na_2CO_3.H_2O$) concentration of about 100 grams/liter to about 200 grams/liter, i.e., having a carbonate ion concentration of about 0.8 Normal to about 1.6 Normal.

Preferably, the aqueous carbonate ion concentrate has a carbonate ion concentration of about 0.85 Normal to about 1.35 Normal, which in the case of sodium carbonate monohydrate means that the concentrated aqueous solution contains about 111 grams/liter to about 170 grams/liter of sodium carbonate monohydrate. The concentrate is then subsequently diluted with conditioned water in a water-to-concentrate volume ratio of about 28:1 for introduction into mixing chamber 12. The diluted aqueous carbonate solution is combined with the concentrated acid solution in a volume ratio of about 34:1, respectively to provide a dialysate having a bicarbonate ion concentration usually in the range of about 35 to about 50 milliequivalents per liter. Other mixing schemes and dilution ratios can also be used as long as the formation of undesirable precipitates is avoided, however.

Figure 2:
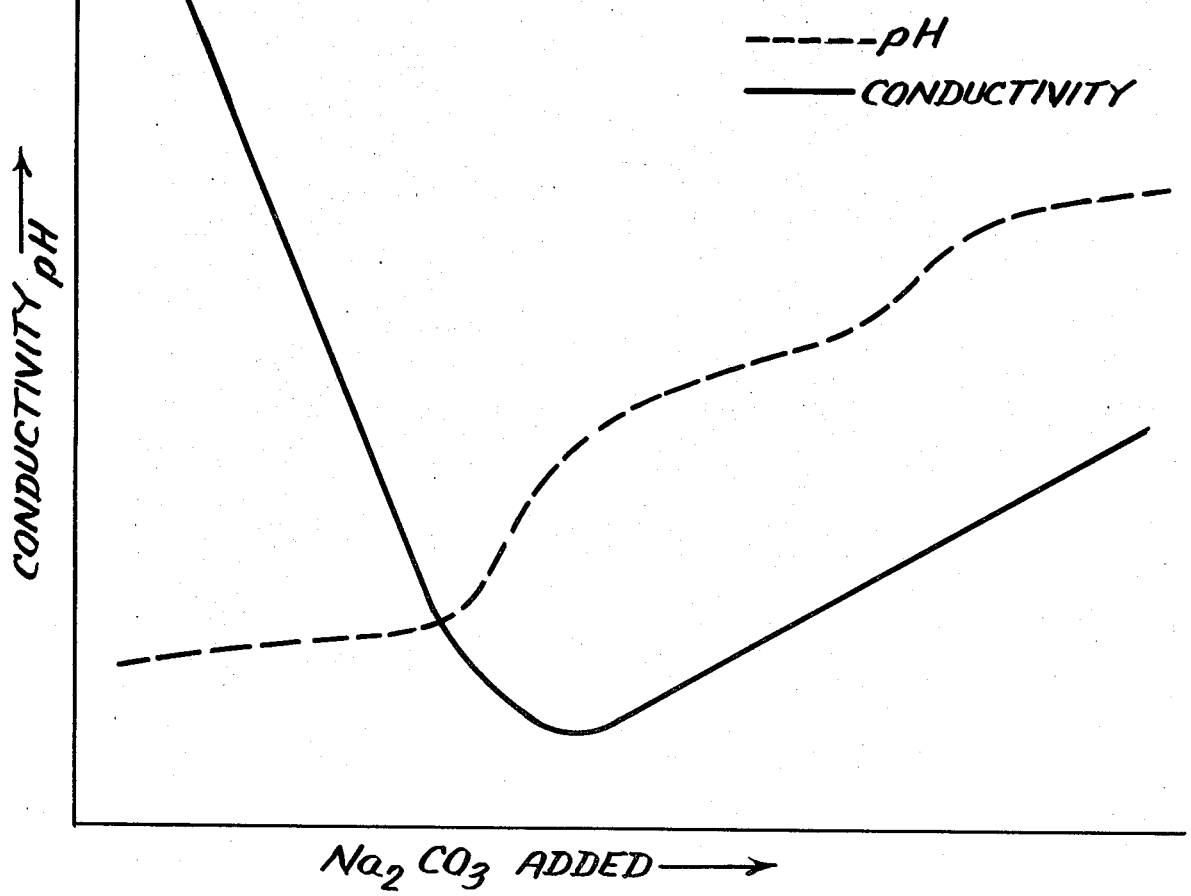
FIG. 2 is a graphical representation of the conductivity and pH of an aqueous stream obtained by combining an aqueous sodium carbonate stream and an aqueous hydrochloric acid-containing stream.

While the conductivity measurement usually provides a good indication of bicarbonate ion concentration in the solution that is used for hemodialysis, it has been found that the conductivity of the aqueous bicarbonate solution formed as a result in mixing chamber 12 passes through a minimum as the hydrogen ion activity of the bicarbonate solution decreases in the range of an apparent pH value of about 4 to about 6 and subsequently again increases. This is schematically illustrated in FIG. 2. Inasmuch as dialysis is usually carried out at about physiological pH, and an acidic dialysate is not only undesirable from a therapeutic standpoint but may also damage the dialysis membranes, it is important to guard against a dialysate that is too acid.

To this end pH probe 13, or a similar potentiometric means for monitoring the hydrogen ion activity of the aqueous solution leaving mixing chamber 12, is provided downstream from mixing chamber 12 in addition to conductivity probe 14. pH Probe 13 provides an output that is indicative of hydrogen ion activity in the produced solution, and conductivity probe 14, in turn, provides an output that indicates the conductivity of this solution. Both of these outputs are transmitted to valve control means 15 which is suitably programmed to energize by-pass valve 16 so as to divert to drain any portion of the produced bicarbonate solution when the value of the outputs of either probe 13 or probe 14 deviates from a set magnitude by a predetermined degree. That is, under normal operating conditions an aqueous bicarbonate-containing dialysate is conveyed via conduit 17 to a dialysis cell (not shown), but a predetermined deviation in either pH or conductivity will cause by-pass valve 16 to be energized so as to divert the dialysate to drain via conduit 18.

A preferred proportioning system embodying the present invention that may be used in conjunction with an existing dialysis machine so as to utilize some of the machine components that are already present is illustrated in FIG. 3. To this end, auxiliary unit 20 may contain the dispensing system for the aqueous carbonate solution together withe the indicator and control means for the entire proportioning system embodying this invention while a dialysis machine 21 may be equipped with the remainder of the necessary system components.

The functions performed by auxiliary unit 20 include metering of a controlled amount of concentrated aqueous carbonate solution and combining the metered amount with conditioned water, monitoring of conductivity of the resulting dilute aqueous carbonate solution, monitoring the hydrogen ion activity or pH of the dialysate produced, and protecting the patient against errors induced by equipment malfunction, improper starting solutions, and the like occurrences.

Auxiliary unit 20 includes carbonate concentrate pump 22, a metering pump usually having a capacity of zero to about 50 milliliters/minute, and associated pump control means 24, mixing unit or tank 26, temperature-compensated conductivity probes 28 and 30, and appropriate indicators and controls in module 32, including, for example, a conductivity meter, a pH meter, various indicator lights, audio alarms, and the like. Carbonate concentrate pump 22 communicates with carbonate concentrate source 34 by means of flexible conduit 36 and functions to convey a concentrated aqueous carbonate solution to mixing tank 26 via conduit 37. The concentrated aqueous carbonate solution is diluted in mixing tank 26 with conditioned water supplied through flexible conduit 38 at a predetermined, substantially constant volumetric rate. The resulting dilute aqueous carbonate solution (about 28:1 dilution in case of sodium carbonate monohydrate solution) is then fed to proportioning unit 40 in dialysis machine by means of conduit 39. Conditioned water can be supplied, usually at a constant temperature of about 98° F. (37° C.), to mixing tank 26 directly from an external source (not shown) by means of a separate pump means (not shown) via conduits 81, 82 and 38 which together with valves 83 and 84 form a continuous confined flow passageway for the conditioned water. Alternatively, and depending on the particular proportioning unit 40 that is installed in the dialysis machine 21, all or a portion of the total amount of conditioned water needed to constitute the dialysate can be passed through proportioning unit 40 with the amount needed for preparing a dilute carbonate solution being pumped to mixing tank 26 via conduits 85 and 86 upon appropriate setting of valves 83 and 84 while utilizing the pumping device or devices normally present in proportioning unit 40.

Temperature-compensated conductivity probe 28 is provided associated with mixing tank 26 and controls operation of pump 22 to produce the diluted aqueous carbonate solution. Probe 28 provides an output signal that is received by pump control means 24 and regulates the rate of introduction of the concentrated carbonate solution into mixing tank 26. The purpose of this conductivity control loop is to maintain a substantially constant carbonate ion concentration in the diluted aqueous carbonate solution. Inasmuch as conductivity is a function of concentration as well as solution temperature, a temperature-compensated signal to pump control 24 is desirable. Preferably, all conductivity values are referenced to 98° F. (37° C.).

Alternatively, the signal or signals emanating from probe 28 can be first transmitted to control circuitry module 32 and then an appropriate signal transmitted to pump control means 24.

Conductivity probe 30 is also temperature-compensated and provides an output signal that is received by indicator and control circuitry module 32 which, in turn, provides a visual and/or audio indication of the conductivity of the diluted carbonate solution stream leaving auxiliary unit 21, and flowing to proportioning unit 40, for example. Additionally, module 32 is operable connected and supplies information to main control circuitry module 42 via cable 44. The redundancy afforded by a pair of temperature-compensated conductivity probes provides a further assurance that the diluted carbonate solution fed to dialysis machine 21 for further compounding into a dialysate solution has the desired concentration at all times.

Stabilization chamber or tank 58 is provided between probes 28 and 30 in order to stabilize the diluted carbonate solution and also to provide a reserve supply. A chamber volume of about 250 cubic centimeters is usually adequate for this purpose; however, larger or smaller volume chambers can be used as required in any given instance.

Aqueous acid concentrate source 46 supplies the aqueous acid concentrate to proportioning unit 40 by means of flexible conduit 48. Proportioning unit 40 meters the diluted carbonate solution and the acid concentrate solution to provide a stream of each solution in a predetermined volume ratio, usually about 34:1, to mixing tank 50. The volume ratio may vary, however, depending on the type of proportioning unit used and the concentration of the diluted aqueous carbonate solution used in any given instance. In any event, each stream is supplied to mixing tank 50 separately, e.g., the dilute carbonate stream is supplied through conduit 52 and the acid concentrate stream is supplied through conduit 54. Deaeration pump 56 can be optionally provided in conduit 52 to remove any air that may be present in the diluted carbonate stream. If desired, the aqueous acid concentrate can also be diluted with conditioned water in proportioning unit 40 before being combined with the dilute carbonate stream. Also, with some dialysis machines conduit 39 can lead directly to pump 56, and conduit 52 can be eliminated between proportioning unit 40 and pump 56.

Mixing tank 50 can be a vortex-type mixing chamber so as to rapidly achieve good and thorough mixing of the incoming streams. From mixing tank 50 the combined streams are conveyed further by means of conduit 62, equipped with air trap 59, to a dialysis cell (not shown) for use in a dialysis cell or unit as the dialysate for dialyzing a patient.

As pointed out hereinabove, it is important not only to monitor the conductivity of the dialysate but also the hydrogen ion activity thereof. For this purpose pH sensor 64 and dialysate conductivity probe 66 are provided downstream from dialysate mixing tank 50 and air trap 59. An output signal generated by pH sensor 64 can be transmitted to indicator and control module 32, and an output signal generated by dialysate conductivity probe 66 is transmitted to main control module 42. Alternatively, both of these output signals can be first transmitted to main control module 42 and appropriate information thereafter transmitted to indicator and control module 32 via cable 44. Depending on the type of pH sensor utilized, a temperature sensor-compensator may also be desirable for the pH sensor.

Inasmuch as the conductivity of an aqueous solution is a function of temperature, temperature probe 68 is provided in conduit 62 and generates an output signal indicative of dialysate temperature at the time the conductivity thereof is measured. The output signal from temperature probe 68 is also transmitted to control module 42 where it is integrated with the other received signals using appropriate circuitry, e.g., a suitably programmed microprocessor, or the like. Temperature probe 68 can be a thermistor, a thermocouple, or a similar temperature sensing device. The output signal from temperature probe 68 can also be used to compensate the output signal from pH probe or sensor 64 as well as to regulate the heat input to the stream of conditioned water that enters the present system via conduit 81.

The output signal from pH sensor 64 can be further utilized to control the operation of carbonate concentrate pump 22 alone or together with the output signal from conductivity and temperature probe 28, as desired.

By-pass valve 70 is positioned in conduit 62 downstream of probes 64, 66 and 68 and is operably associated with control module 42 so that any deviation from normal operating conditions or dialysate characteristics will cause by-pass valve 70 to be actuated so as to divert the dialysate stream passing through conduit 62 to drain via drain passageway 72 and to interrupt the dialysate flow to a dialysis cell (not shown).

Turbidity detector 87 in drain passageway 72 serves to detect any undesirable precipitate that may be present. Detector 87 can be a conventional blood leak detector usually present in dialysis machines.

The foregoing description and the accompanying drawings are intended as illustrative and are not to be taken as limiting. Still other variations and rearrangements of system components without departure from the spirit and scope of the present invention are possible and will readily present themselves to those skilled in the art.

We claim:
1. A proportioning system for compounding a bicarbonate-containing dialysate suitable for use in a dialysis cell which system comprises
    a source of aqueous sodium carbonate concentrate;

a source of aqueous hydrochloric acid-containing concentrate;

a source of physiologically tolerable water;

means for commingling an aqueous stream from each of said sources to provide a bicarbonate-containing dialysate stream for said dialysis cell;

means for monitoring hydrogen ion activity in the produced dialysate and providing an output indicative of said activity;

conductivity sensing means for monitoring the conductivity of the produced dialysate and providing an output indicative of said conductivity; and flow control means operably associated with the means for monitoring hydrogen ion activity and the conductivity sensing means, individually responsive to each of said outputs and interrupting normal flow of said dialysate when the value of either of said outputs deviates from a set magnitude by a predetermined amount.

2. The system in accordance with claim 1 wherein said means for monitoring hydrogen ion activity is a pH probe.

3. The system in accordance with claim 1 wherein said flow control means is a by-pass valve adapted to divert the dialysate to drain.

4. A proportioning system for compounding in situ a bicarbonate-containing dialysate suitable for use in a dialysis cell and comprising:

a source of aqueous carbonate ion concentrate;

a source of aqueous hydrochloric acid-containing concentrate;

a source of condition water;

a first mixing tank means for combining a stream of said aqueous carbonate ion concentrate with a stream of said water to produce a diluted aqueous carbonate solution;

metering pump means for introducing said aqueous carbonate ion concentrate stream into said first mixing tank means;

first temperature-compensated conductivity probe associated with said first mixing tank means and operably connected to said metering pump means to control the rate at which said aqueous carbonate ion concentrate is introduced into said first mixing tank means;

a stabilization chamber downstream from said first mixing tank means for receiving said diluted aqueous carbonate solution;

second temperature-compensation conductivity probe downstream from said stabilization chamber for monitoring conductivity of the stream of diluted aqueous carbonate solution withdrawn from said stabilization chamber and providing an output signal representative of the conductivity of said diluted aqueous carbonate stream;

second mixing tank means for combining the stream of diluted aqueous carbonate solution withdrawn from said stabilization chamber with a stream of said aqueous acid concentrate to form a stream of said bicarbonate-containing dialysate;

means for monitoring hydrogen ion activity in said dialysate stream and providing an output signal representative of said hydrogen ion activity;

dialysate conductivity sensing means for monitoring conductivity of said dialysate stream and providing an output signal representative of the conductivity thereof;

control means operably associated with at least said second temperature-compensated conductivity probe, said means for monitoring hydrogen ion activity and said dialysate conductivity sensing means to receive the respective output signals therefrom and to generate a control signal in response thereto; and dialysate flow control means downstream from said means for monitoring hydrogen ion activity and said dialysate conductivity sensing means and adapted to interrupt flow of said dialysate stream to the dialysis cell in response to said control signal.

5. The proportioning system in accordance with claim 4 wherein said means for monitoring hydrogen ion activity is a pH probe.

6. The proportioning system in accordance with claim 5 wherein the pH probe is temperature-compensated.

7. A proportioning system for compounding in situ a bicarbonate-containing dialysate suitable for hemodialysis and comprising:

a source of aqueous carbonate ion concentrate;

a source of aqueous hydrochloric acid-containing concentrate;

a source of conditioned water; mixing tank means for combining a stream of said aqueous carbonate ion concentrate with a stream of conditioned water from said respective sources to produce a diluted aqueous carbonate solution;

carbonate metering pump means for introducing said stream of aqueous carbonate ion concentrate into said mixing tank means;

stabilization chamber downstream from said mixing tank means for receiving said diluted aqueous carbonate solution;

temperature-compensated conductivity probe downstream from said stabilization chamber for monitoring conductivity of the stream of diluted aqueous carbonate solution withdrawn from said stabilization chamber and providing an output signal representative of the conductivity of said diluted aqueous carbonate stream;

dialysate mixing tank means for combining said withdrawn stream of diluted aqueous carbonate solution with a stream of said aqueous acid concentrate to form a stream of said bicarbonate-containing dialysate;

means for monitoring hydrogen ion activity in said dialysate stream and providing an output signal representative of said hydrogen ion activity;

metering pump control means associated with said carbonate metering pump means and responsive to said output signal from said means for monitoring hydrogen ion activity;

dialysate conductivity sensing means for monitoring conductivity of said dialysate stream and providing an output signal representative of the conductivity thereof;

control means operably associated with said temperature-compensated conductivity probe, said means for monitoring hydrogen ion activity and said dialysate conductivity sensing means, to receive the respective output signals therefrom and to generate a control signal in response thereto; and dialysate flow control means downstream from said means for monitoring hydrogen ion activity and said dialysate conductivity sensing means, and adapted to interrupt flow of said dialysate stream to a dialysis cell in response to said control signal.

8. The proportioning system in accordance with claim 1 wherein the means for monitoring hydrogen ion activity is a pH probe.

9. The proportioning system in accordance with claim 8 wherein the pH probe is temperature-compensated.

10. A device for diluting an aqueous carbonate solution to provide a carbonate-ion containing solution suitable for combining with an aqueous acid solution to produce a dialysate, which comprises:
mixing tank means for receiving and combining an aqueous carbonate solution and a stream of conditioned water to produce a diluted aqueous carbonate solution;
water conduit means for providing communication between said mixing tank means and a conditioned water source;
metering pump for dispensing the aqueous carbonate solution to the mixing tank means, communicating with said mixing tank means and adapted to communicate with a source of the aqueous carbonate solution;
stabilization chamber for receiving the diluted aqueous carbonate solution downstream from said mixing tank means and communicating therewith;
first conductivity probe associated with said mixing tank means, determining the conductivity of the diluted aqueous carbonate solution in said mixing tank means and providing an output signal representative of the conductivity thereof;
metering pump control means operably associated with said metering pump and with said first conductivity probe to control the dispensing rate of said metering pump in response to the output signal from said first conductivity probe;
exit conduit means for conveying the diluted aqueous carbonate solution from said stabilization chamber and communicating therewith;
second conductivity probe in said exit conduit means for monitoring conductivity of the diluted aqueous carbonate solution exiting said stabilization chamber and providing an output signal representative of the conductivity of said exiting solution; and
indicator means operably associated with said second conductivity probe to receive the output signal therefrom and providing a discernible indication of the conductivity of said exiting solution.

11. The device in accordance with claim 10 wherein said first and second conductivity probes are temperature-compensated.

12. The device in accordance with claim 10 wherein said metering pump has a dispensing capacity of zero to about 50 milliliters per minute.

13. The device in accordance with claim 10 wherein said exit conduit also communicates with a proportioning unit in a dialysis machine.

14. A method for preparing a bicarbonate dialysate in situ from bacteriorstatic starting solutions which comprises the steps of
providing an aqueous sodium carbonate solution;
providing an aqueous hydrochloric acid-containing solution;
providing a source of physiologically-tolerable water;
diluting said aqueous sodium carbonate solution with said water to produce a diluted sodium carbonate solution that will not cause a precipitate when combined with said aqueous hydrochloric acid containing solution; and
combining said diluted sodium carbonate solution with said hydrochloric acid containing solution in a predetermined volumetric ratio while monitoring hydrogen ion activity and conductivity of the resulting dialysate.

15. The method in accordance with claim 14 wherein said sodium carbonate solution has a carbonate ion concentration of about 0.8 Normal to about 1.6 Normal.

16. The method in accordance with claim 14 wherein said sodium carbonate solution has a carbonate ion concentration of about 0.85 Normal to about 1.35 Normal.

17. The method in accordance with claim 14 wherein said aqueous hydrochloric acid-containing solution has a hydrogen ion concentration of about 11 to about 12 Normal.

18. The method in accordance with claim 14 wherein said aqueous sodium carbonate solution is diluted by comining a stream thereof with a stream of physiologically tolerable water at a volumetric rate determined by conductivity of the diluted solution.

19. The method in accordance with claim 14 wherein said aqueous sodium carbonate solution is diluted by combining a stream thereof with a stream of physiologically tolerable water at a volumetric rate determined by pH of the resulting dialysate.

* * * * *

UNITED STATES PATENT AND TRADEMARK OFFICE
CERTIFICATE OF CORRECTION

PATENT NO. : 4,399,036
DATED : August 16, 1983
INVENTOR(S) : Albert L. Babb and Belding H. Scribner It is certified that error appears in the above-identified patent and that said Letters Patent is hereby corrected as shown below:

Col. 5, lines 34-35, "operable" should be -- operably --.

Col. 7, line 50, "temperature-compensation" should be -- temperature-compensated --.

Col. 9, line 4, "claim 1" should be -- claim 7 --.

Col. 10, line 42, "comining" should be -- combining --.

Signed and Sealed this

Third Day of January 1984

[SEAL]

Attest:

GERALD J. MOSSINGHOFF

Attesting Officer        Commissioner of Patents and Trademarks